US004001565B2

United States Statutory Invention Registration [19]

[11] Reg. Number: H1565

Brodof et al.

[45] Published: Jul. 2, 1996

[54] SUPERABSORBENT, CONTINUOUS FILAMENT WEB

[76] Inventors: Terry A. Brodof, 7714 Quail Hill Rd., Charlotte, N.C. 28210; Ronald O. Bryant, 1100 Ardsley Rd., Charlotte, N.C. 28207; Harold W. Davis, 1551 Ovenbrook Dr., Gaffney, S.C. 29340

[21] Appl. No.: 290,260

[22] Filed: Aug. 15, 1994

[51] Int. Cl.[6] ..... A61F 13/15

[52] U.S. Cl. ..... 604/368; 156/305

[58] Field of Search ..... 604/358, 365, 604/367, 368; 156/296, 167, 308.6, 305

[56] References Cited

U.S. PATENT DOCUMENTS

| | | | |
|---|---|---|---|
| 3,686,024 | 8/1972 | Nankee | 604/368 |
| 3,966,679 | 6/1976 | Gross | 260/47 |
| 4,187,342 | 2/1980 | Holst et al. | 604/365 |
| 4,444,830 | 4/1984 | Erickson | 428/246 |
| 4,468,428 | 8/1984 | Early et al. | 428/221 |
| 4,600,462 | 7/1986 | Watt | 156/296 |
| 5,217,445 | 6/1993 | Young et al. | 604/368 |
| 5,300,192 | 4/1994 | Hansen et al. | 156/305 |
| 5,352,480 | 10/1994 | Hansen et al. | 604/368 |
| 5,362,766 | 11/1994 | Hopkins, Jr. et al. | 523/105 |

*Primary Examiner*—Harold J. Tudor

[57] ABSTRACT

The present invention is directed to a novel absorbent article that includes immobilized superabsorbent particulate in a fiber structure of high integrity. More particularly, a continuous filament web loaded with the superabsorbent particulate, is provided. Cellulose ester tow having crimped filaments, is advantageously used as a starting material. Also provided is a process for adhering superabsorbent particulate to opened tow by use of a tackifying agent.

17 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SUPERABSORBENT, CONTINUOUS FILAMENT WEB

FIELD OF THE INVENTION

This invention relates to a superabsorbent web based upon continuous filament tow.

BACKGROUND OF THE INVENTION

Superabsorbent polymers are polymeric materials capable of absorbing many times their own weight of water and other liquids. Commercially, these polymeric materials are used as additives to increase the absorbency of disposable articles such as diapers, adult incontinence pads, feminine hygiene pads, tampons and the like.

Superabsorbent polymers are commonly used as powders or granules. If not immobilized, the powdered material may bunch up or agglomerate, resulting in uneven absorptive capacity or discomfort, or may become air-borne, resulting in health risks due to swelling of particulate within human air passages.

A variety of methods have been suggested to provide immobilization of superabsorbent polymer (SAP) particulate. PCT application WO 90/11181 describes a fiber product in which discontinuous fibers are coated using a mist of a liquid binder material, and superabsorbent particulate is applied to the binder-wetted fibers. Particulate adhesion is provided by drying or heating. Also described is forming a mixture of SAP particulate in a melt. European Patent Application 425,269 describes use of such a melt for melt-spinning fiber which may be cellulose acetate fiber. U.S. patent application Ser. No. 07/805,538, filed on Dec. 11, 1991, describes forming a suspension of SAP particles in a solvated matrix material which may be a cellulose ester, for extruding or casting.

In addition, U.S. Pat. Nos. 3,966,679 to Gross, 4,444,830 to Erickson, 4,600,462 to Watt and 4,468,428 to Early et al illustrate absorbent materials including SAP as an additive. Generally speaking, in this type of prior work, a binder is also used, or SAP is formed in situ on a substrate. In the Watt patent, an air laid, cellulosic fiber web is treated with a hydrophobic binder and a hydrophile. Erickson and Gross describe coating an aqueous polymer solution including a cross-linking agent, onto a substrate to form a coating of SAP. Erickson coats a fibrous material which is thereafter mechanically worked to form a discontinuous fiber matrix. Erickson suggests starch/graft copolymers may also be used. The coating of Gross may be continuous or discontinuous.

Continuous filament, cellulose ester tow having crimped filaments, is commercially available from Hoechst Celanese Corporation of Charlotte, N.C. For cigarette filter applications, the tow is opened and thereafter treated with triacetin or a similar agent to build hardness, and the treated tow is formed into a filter.

Manufacturers of absorbent articles are striving to make ever thinner absorbent products while maximizing fluid absorption. In the past, these efforts have been hampered by: pad having poor strength in the machine direction that limits production rates and in-use performance; and lack of immobilization of the superabsorbent material. The prior art discussed above is directed primarily to the solution of the latter problem.

Accordingly, despite advances in absorbent products, an improved absorbent article including superabsorbent particulate is needed. Beneficially, the superabsorbent particulate would be immobilized in a high integrity web. Advantageously, immobilization would be achieved without deleteriously affecting absorptive capacity. Accordingly, there is a need for an improved process for providing superabsorbent fiber loaded with immobilized superabsorbent particulate, and yet that maintains absorptive capacity.

SUMMARY OF THE INVENTION

In accordance with the present invention, an improved absorbent article may be advantageously based upon continuous filament tow having crimped filaments. In accordance with the invention, the tow is beneficially moisture-absorbent and biodegradable. Advantageously, a cellulose ester tow, such as cellulose acetate, is used. Conveniently, the absorbent article also may include a matrix of discontinuous absorbent fibers, in particular cellulosic fibers. This invention enables one to make a thinner absorptive product because the invention is directed to superabsorbent particulates that are immobilized in a web of continuous filaments.

In accordance with the invention, continuous filament tow is opened and superabsorbent particulate is adhered to the surface of fibers thereof to provide a superabsorbent, continuous filament web loaded with immobilized superabsorbent particulate. Filament crimp enhances separation between filaments, beneficially providing increased available filament surface area for particulate adherence. Advantageously, the loading of the particulate may be about 50 to 95 wt. %, based on the combined weight of the particulate and tow fibers. The particulate-loaded, continuous filament web has high structural integrity.

Use of a binder for immobilization of the particulate would generally have an adverse effect upon absorptive capacity. Reduction in absorptive capacity may result, for instance, from coating of the particulate by the binder. Therefore, in accordance with the present invention, adherence of the particulate to the tow fibers is beneficially effected in a manner that maintains absorptive capacity. To maintain the needed superabsorbency and yet provide for particulate immobilization, conventional hydrophobic and hydrophilic binders are avoided, and in place thereof, an agent that tackifies the tow, superabsorbent particulate, or tow and superabsorbent particulate is advantageously used.

In an advantageous process for making a superabsorbent fiber web in accordance with the invention, superabsorbent particulate and an effective amount of the tackifying agent are applied to opened, continuous filament tow. Beneficially, the tackifying agent may be applied to the opened tow prior to the particulate, in which case the tackifying agent may tackify the fibers of the tow or the particulate. Alternatively, the particulate and tackifying agent may be simultaneously applied to the opened tow.

The tackifying agent may be volatile or non-volatile. Use of a non-volatile tackifying agent typically results in a particulate-loaded web that includes the tackifying agent.

DETAILED DESCRIPTION OF THE INVENTION

Figure 1:
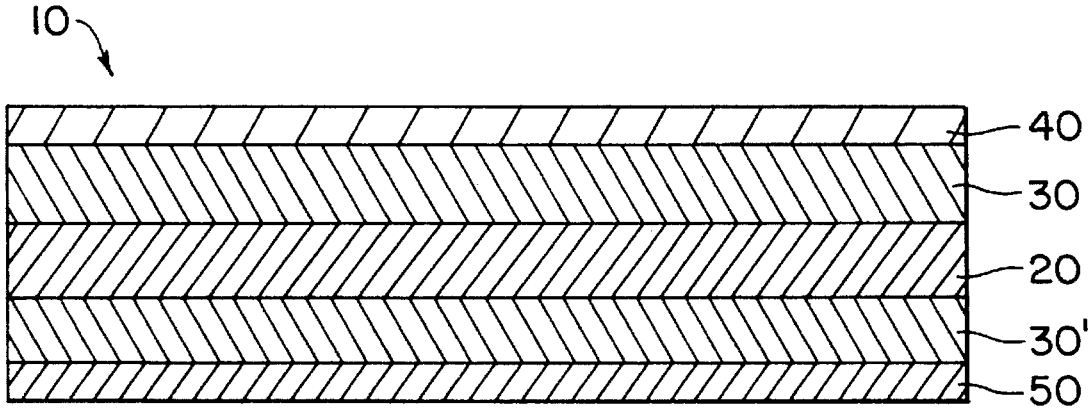
FIG. 1 illustrates an absorbent product in accordance with the present invention.

As indicated above, in accordance with the invention, superabsorbent particulate is immobilized in a high integrity web. Moreover, immobilization may be achieved without use of a conventional hydrophilic or hydrophobic, polymeric binder. Also, immobilization may be provided without forming a mixture of superabsorbent particulate in a molten matrix material, or a suspension of superabsorbent particulate in a solvated matrix material. In other words, immobilization is beneficially effected in a manner that avoids coating of the particulate, degradation of the particulate, and melting or solvation of the matrix.

By the invention, substantial retention of absorbency is achieved. By the term "substantial retention of absorbency", as used herein, is meant that the superabsorbent material retains at least about 50% of its original liquid absorption capacity. Beneficially, retention of greater than about 90% of original absorbency may be achieved.

Referring to the drawing, there is shown an absorbent article 10 in accordance with the present invention. Article 10 includes a superabsorbent, continuous filament web 20, and a matrix 30 of discontinuous absorbent fibers. Conveniently, the discontinuous fibers are cellulosic fibers, as conventionally used in absorbent articles.

Absorbent article 10 further includes a moisture-permeable layer 40 overlaying continuous filament web 20, and a moisture-impermeable layer 50 underlaying continuous filament web 20. As shown, web 20 may be sandwiched between matrix 30 and a like matrix 30'. In use, the moisture-permeable layer 40 is typically intended for direct contact with the body of a user.

A sheet, film or membrane may be used to provide layer 40, as well as layer 50. Further details of matrix 30 and layers 40,50 are conventional, and are therefore omitted from this description for sake of brevity. Specifics of superabsorbent, continuous filament web 20, are discussed in detail below.

Absorbent article 10 may be provided in many forms, and may be disposable or non-disposable. Absorbent articles within the scope of this invention, may be used for many purposes, and include diapers, incontinence pads, feminine hygiene pads, tampons and the like.

In accordance with the present invention, improved absorbent articles are advantageously based upon continuous crimped filament tow. Specifically, a superabsorbent, continuous filament web is prepared therefrom. This fiber structure has high structural integrity, and as such, is distinct from a matrix of discontinuous fibers described as fluff by prior art such as WO 90/11181 and Erickson. The high structural integrity enables the production of stronger webs than those formed from discontinuous fibers. Stronger webs enable the production of thinner absorbent pads. By the term "continuous filament", as used herein, is meant a plurality or bundle of continuous filaments.

Beneficially, cellulose ester tow is used. Non-limiting examples of suitable cellulose esters include cellulose acetate, cellulose propionate, cellulose butyrate, cellulose caproate, cellulose caprylate, cellulose stearate, highly acetylated derivatives thereof such as cellulose diacetate, cellulose triacetate and cellulose tricaproate, and mixtures thereof such as cellulose acetate butyrate. Characteristics defining an appropriate cellulose ester, include the ability to absorb moisture and biodegradability, and are influenced not only by the substituent groups but also by the degree of substitution. The relationship between substituent groups, degree of substitution and biodegradability is discussed in W. G. Glasser et al, *Biotechnology Progress,* vol. 10, pp. 214–219 (1994), hereby incorporated herein by reference.

As may thus be understood, a continuous filament tow useful in the present invention, is beneficially moisture-absorbent and biodegradable. Accordingly, cellulose acetate tow is typically preferred for use in the invention. By comparison, a thermoplastic tow such as polyester, polypropylene or polyamide tow, lacks moisture-absorbency and biodegradability.

Typically, dpf of the tow fiber will be in the range of about 1 to 9, preferably about 3 to 6. For the same weight product, filaments of lower dpf may provide increased surface area and increased moisture absorption. Total denier may vary within the range of about 20,000 to 60,000, depending upon the process used.

Beneficially, tow having crimped filaments is used. Crimp aids in opening. Separation of filaments resulting from bloom, advantageously results in increased available filament surface area for superabsorbent material immobilization and increased moisture absorption. Gel blocking may be reduced. As therefore may be understood, more crimp is typically better, with in excess of about 20 crimps per inch being usually preferred. Continuous filament, cellulose ester tow having crimped filaments with about 25 to 40 crimps per inch, is commercially available from Hoechst Celanese Corporation, Charlotte, N.C.

If desired, a superabsorbent, absorptive pad of multiple layer thickness, may be provided. To this end, the tow may be, for instance, lapped or crosslapped in accordance with conventional procedures. In this way, a superabsorbent, absorptive material of a desired weight and/or thickness may be provided. The specific weight or thickness will depend upon factors including the particular end use.

Superabsorbent materials suitable for use in the present invention, include conventional superabsorbent polymers, as that term is commonly applied in the art. Examples of such materials are water swellable polymers of water soluble acrylic or vinyl monomers crosslinked with a polyfunctional reactant. Also included are starch modified polyacrylic acids and hydrolyzed polyacrylonitrile and their alkali metal salts. A more detailed recitation of superabsorbent polymers is found in U.S. Pat. No. 4,990,541 to Nielsen, incorporated herein by reference.

Commercially available SAPs include a starch modified superabsorbent polymer available under the tradename SANWET® from Hoechst Celanese Corporation, Portsmouth, VA. SANWET® is a starch grafted polyacrylate sodium salt. Other commercially available SAPs include a superabsorbent derived from polypropenoic acid, available under the tradename DRYTECH® 520 SUPERABSORBENT POLYMER from Dow Chemical Company, Midland Mich.; AQUA KEEP manufactured by Seitetsu Kagaku Co., Ltd.; ARASORB manufactured by Arakawa Chemical (U.S.A.) Inc.; ARIDALL 1125 manufactured by Chemdall Corporation; and FAVOR manufactured by Stockhausen Inc.

A suitable particle size for the superabsorbent material varies greatly. However, typically, use of a fine particulate rather than a coarse particulate, produces advantages as illustrated in Example 13. Beneficial is a fine particulate that passes through an about 200 mesh screen.

Generally speaking, it is advantageous for the continuous filament structure to be present in a minor amount compared to the amount of superabsorbent particulate. Accordingly, although a continuous filament web including immobilized particulate, may in accordance with the invention include from about 5% to 95% by weight of the continuous filaments, it is generally preferable that no more than about 50 wt. % of the particulate-loaded web, be fiber.

Conversely, the particulate-loaded web may include from about 5 to 95% by weight of superabsorbent particulate, based on the combined weight of the particulate and of the continuous filament. However, generally speaking, the higher the loading of the particulate, the better a superabsorbent fiber web in accordance with the present invention, functions. Thus, the continuous filament web may beneficially be loaded with about 50 to 95% by weight of the particulate, preferably at least about 75% by weight.

As indicated, it is an object of the present invention to immobilize superabsorbent particulate in a high integrity, fiber structure with substantial retention of absorbency. In accordance with the present invention, continuous filament tow is opened in a conventional manner, and a tackifying agent is used for adherence of the particulate to the surface of filaments of the opened tow.

By the term "tackifying agent", as used herein, is meant any agent suitable for adhering superabsorbent particulate to the tow fibers, by making the particulate or tow fibers sticky, by a solvating or wetting action upon particulate or fiber surface. Excluded from the term are conventional hydrophobic and hydrophilic binders that would interpose an adhesive layer or spot of adhesive between particulate and fiber surface, and in addition coat particulate as well as fiber.

Volatile or non-volatile liquids may be used as the tackifying agent. Useful volatile liquids include water, and hydrocarbons such as low molecular weight ketones, halogenated hydrocarbons, esters and ethers, preferably having a boiling point of about 100° C. or less, very preferably of about 80° C. or less, at atmospheric pressure. Water may be advantageously used to tackify the particulate. Suitability of a particular liquid hydrocarbon as a tackifying agent, depends upon the tow selected. Examples of volatile hydrocarbon liquids capable of tackifying cellulose ester fiber, include acetone, methyl ethyl ketone, methyl acetate, ethyl acetate, propyl acetate, methyl formate, ethyl formate, propyl formate, glacial acetic acid, methylene chloride, tetrahydrofuran, formic acid, and mixtures thereof; and include combinations thereof with a minor amount, typically about 5 to 30 vol. %, of other volatile liquids preferably having a boiling point of about 100° C. or less at atmospheric pressure, such as ethanol, water and halogenated hydrocarbons. Exemplary useful combinations include acetone/water and methylene chloride/ethanol.

Non-volatile liquids useful as tackifying agents, include glycerol derivatives, cyclohexanone, and benzyl alcohol. Exemplary suitable glycerol derivatives include glyceryl triacetate, known as triacetin, triethylglycerol diacetate, and glycol monoethyl ether acetate.

By the term "non-volatile" as used herein with respect to a tackifying agent, is meant having a boiling point at atmospheric pressure, in excess of about 140° to 150° C., especially in excess of about 200° C. However, the term does not imply that the tackifying agent may not be removed by a drying step; rather, generally speaking, more intensive drying conditions are necessary.

Advantageously, the tackifying agent may produce fiber-fiber adhesion, thereby further enhancing structural integrity. Illustrative is triacetin. As may be understood, the tackifying agent is non-polymeric and is thus completely unlike conventional polymeric binders.

The amount of the tackifying agent to be used, varies depending upon the tackifying agent, superabsorbent particulate and tow selected. When triacetin, SANWET® and cellulose acetate tow are used, a useful percentage of triacetin typically ranges, on a weight basis, from about 1 to 25. More preferred is about 1–10% on a weight basis, and most preferred is about 2–7% on a weight basis. In any event, an amount will be used that is effective to make the particulate or tow fibers sticky, by a solvating or wetting action upon particulate or fiber surface. Importantly, the amount or level is controlled to prevent total solvation of fiber. Control may be provided by use of a diluent for the tackifying agent. For example, when triacetin or methyl ethyl ketone is selected for tackifying cellulose acetate tow, methanol may be used as a diluent. Depending upon the tow fiber and tackifying agent, an about 7.5 to 15:1 ratio of diluent to tackifying agent is generally useful.

The tackifying agent and the superabsorbent particulate may be applied to the fibers of the opened tow, simultaneously or separately. In any event, the tackifying agent is applied under conditions effective to make the particulate or tow fibers sticky, by a solvating or wetting action upon particulate or fiber surface, and to maintain the stickiness until contact is provided between the particulate and tow fibers.

Beneficially, the tackifying agent may be applied to the opened tow prior to the superabsorbent particulate. Application may be by spraying, kiss roll, and so forth. Thereafter, the particulate is beneficially sprinkled onto or sifted onto or otherwise suitably contacted with, the wetted tow. In this case, the tackifying agent may tackify the particulate or fiber surface, or both surfaces. Advantageously, high loadings of particulate in excess of about 75 wt. %, even up to about 90 to 95 wt. %, have been obtained using this procedure.

Alternatively, the tackifying agent and the particulate may be simultaneously applied to the opened tow. Typically, in such case, a suspension of the particulate in the tackifying agent is sprayed, and the tackifying agent functions to make the tow fibers sticky. By the term "suspension" as used herein, is meant a mixture containing a substantially uniform distribution of particulate matter in a liquid carrier.

When spraying is used to apply the tackifying agent, control of the level of tackifying agent may be provided by the output of the spray nozzle used, and in addition, when spraying moving, opened tow, by the line speed of the tow.

A volatile tackifying agent, in particular an organic volatile tackifying agent, may usually be easily removed after particulate immobilization. As a result, a higher weight percent loading of particulate may be obtained than if a non-volatile tackifying agent were chosen, since the weight of unremoved, non-volatile tackifying agent increases the weight of the particulate-loaded web. As may be understood, a comparatively higher temperature and/or increased processing time is needed for removal of a non-volatile tackifying agent.

Removal of the tackifying agent after particulate immobilization, may be by air-drying, application of heat, or any conventional manner. If the tackifying agent or diluent for the tackifying agent, is flammable or toxic, appropriate measures are taken to safely capture the vapors.

Beneficially, the process of the present invention, may be carried out in a continuous matter. Hence, the tow may be continuously opened, and the particulate and tackifier may be continuously applied to the moving, opened tow. As a consequence, improved processing economics result. The particulate-loaded tow may be cut to provide a single layer thickness for use in an absorbent article, or may be made into a multiple layer pad.

The tow may further comprise additives to enhance the physiochemical characteristics of the superabsorbent fiber web and of end use products. Such additives may include antimicrobials. Illustrative is cellulose acetate tow incorporating a chlorinated phenoxy antimicrobial compound, and commercially available under the tradename MICROSAFE AM from Hoechst Celanese Corporation, Charlotte, N.C.

Beneficially, a superabsorbent, cellulose ester web in accordance with the present invention, may reduce diaper rash caused by ammonia. Additionally, the superabsorbent, cellulose ester web may have advantageous compression, elasticity and handling properties for thin, light pads.

The following examples further illustrate the invention. They are presented solely for the purpose of illustration and should not be interpreted as being limitations on the invention. In these examples and throughout this description, all percentages are weight percent unless otherwise stated.

EXAMPLES 1–3

4 dpf×36,000 TD (total denier), continuous filament, cellulose acetate tow having crimped filaments, commercially available from Hoechst Celanese Corporation, Charlotte, N.C., is opened in a conventional manner using a Model AF2 opening system from Korber & Co.

Three lengths of the opened tow are cut, and each length is placed on a piece of previously weighed, kraft paper, and weighed to determine the dry weight. The three lengths are sprayed with a mixture of triacetin, methanol, and starch grafted polyacrylate sodium salt particulate available under the tradename SANWET® IM 3900F from Hoechst Celanese Corporation, Portsmouth, Va.; and then air dried to remove the methanol. The fine particulate is characterized as passing through a 140 mesh screen. The ratio of SAP to triacetin is 1.5:1, and of methanol to triacetin is 8.5:1. The three treated lengths are thereafter each placed on a fresh piece of previously weighed, kraft paper, and weighed to determine the treated weight. The additional weight of each length is calculated; and based on the 1.5:1 ratio of SAP to triacetin in spray mixture, the proportion of the additional weight attributable to triacetin and attributable to SAP particulate is then calculated. The results are shown as "Samples 1–3" in the Table.

Each length is then tested for absorbency and retention of a 0.9% saline solution, using the following test method for determination of Absorbent Ratio and Retention Ratio: Cut and weigh samples (multiple times). Place sample in holder (Gooch crucible, with holes in bottom), and weigh. Place holder in drip tray. Saturate with 10 ml 0.9% saline solution. Measure time for solution to drip through sample. Reweigh to determine the wet weight, and use the wet weight to calculate Absorbent Ratio as ratio of amount of moisture absorbed to dry weight. Centrifuge for 1 minute. Reweigh to redetermine the wet weight, and use the redetermined wet weight to calculate Retained Ratio as ratio of amount of moisture left after centrifuging, to dry weight. The drip time and results are shown in the Table, with each value being an average of four values.

With continued reference to the Table, untreated, opened tow (4.0 dpf×36,000 TD) is evaluated for absorbency and retention, for comparative purposes, and the drip time and results ("Tow Only") are shown in the Table.

EXAMPLES 4–9

With reference to Samples 4–9 of the Table, the treatment procedure of Examples 1–3 is repeated using different proportions of triacetin and SAP particulate in the spray mixture, and thereafter the proportion of the additional weight attributable to triacetin and attributable to SAP particulate is calculated as before. In Samples 4 to 6, the ratio of SAP to triacetin is 1:1, and of methanol to triacetin is 9:1; and in Samples 7–9, the ratio of SAP to triacetin is 1:2, and of methanol to triacetin is 9.5:1. The treated tow lengths are evaluated as before. The drip time and results are shown in the Table.

EXAMPLE 10

With reference to Sample 10, 4.0 dpf×36,000 TD continuous filament, cellulose acetate tow having crimped filaments, commercially available from Hoechst Celanese Corporation, Charlotte, N.C., is opened in a conventional manner as described in Examples 1–3. The opened tow is sprayed with a methanol/triacetin mixture (9:1 ratio). Thereafter, starch grafted polyacrylate sodium salt particulate available under the tradename SANWET® IM 3900 from Hoechst Celanese Corporation, Portsmouth, Va., is applied to the wetted, opened tow by sifting. The particulate is not as fine as that of Example 1 and is characterized as follows: more than 95.5% is 140 mesh or larger in size. The web is thereafter air dried to remove the methanol.

The proportion of the additional weight attributable to triacetin and attributable to SAP particulate is estimated, and based thereon, an 89% loading of superabsorbent polymer particulate adhered to the surface of fibers of the web, is found. The particulate-loaded web is thereafter evaluated as before, and the drip time and results are shown in the Table.

| SAMPLE | % SAP | % FLUFF | % TACKIFYING AGENT | % CONTINUOUS FILAMENT | SALINE DRIP (SEC) | ABSORBENT RATIO | RETAINED RATIO |
|---|---|---|---|---|---|---|---|
| TOW ONLY | 0 | 0 | 0 | 100 | 22.1 | 32.2 | 1.9 |
| SAMPLE 1 | 34 | 0 | 23 (TRI) | 43 | 9.45 | 24.7 | 10.8 |
| SAMPLE 2 | 35 | 0 | 23 (TRI) | 42 | 10.3 | 23.2 | 10.1 |
| SAMPLE 3 | 33 | 0 | 22 (TRI) | 45 | 12.8 | 21.7 | 8.4 |
| SAMPLE 4 | 25 | 0 | 25 (TRI) | 50 | 10.0 | 28.4 | 7.0 |
| SAMPLE 5 | 24 | 0 | 24 (TRI) | 52 | 12.5 | 27.3 | 5.9 |
| SAMPLE 6 | 20 | 0 | 20 (TRI) | 60 | 11.1 | 24.7 | 5.2 |
| SAMPLE 7 | 11 | 0 | 24 (TRI) | 65 | 16.1 | 27.5 | 3.1 |
| SAMPLE 8 | 11 | 0 | 21 (TRI) | 68 | 16.9 | 29.8 | 2.0 |
| SAMPLE 9 | 10 | 0 | 19 (TRI) | 71 | 13.3 | 23.2 | 1.5 |
| SAMPLE 10 | 89 | 0 | 1 (TRI) | 10 | 8.33 | 45.8 | 22.0 |
| SAMPLE 11 | 89 | 0 | 0 (MEK) | 11 | 7.64 | 42.3 | 22.2 |
| SAMPLE 12 | 94 | 0 | 0 (H2O) | 6 | 6.75 | 47.1 | 22.0 |
| SAMPLE 13 | 80 | 0 | 5 (TRI) | 15 | 4.62 | 60.6 | 22.0 |
| C-1* | 45 | 55 | 0 | 0 | 12.6 | 24.9 | 8.4 |

*C-1 IS A COMPARATIVE PRODUCT
(SAP) - Superabsorbent Polymer, (TRI) - Triacetin, (MEK) - Methyl Ethyl Ketone, (H2O) - Water

EXAMPLE 11

With reference to Sample 11, the treatment procedure of Example 10 is repeated, except that the opened tow is sprayed with a mixture of methanol and methyl ethyl ketone (9:1 ratio). After the particulate is applied, the methanol and methyl ethyl ketone are removed by drying. A superabsorbent, continuous filament web having an 89% loading of superabsorbent polymer particulate adhered to the surface of fibers of the web, is thereby produced. The particulate-loaded web is evaluated as before, and the drip time and results are shown in the Table.

EXAMPLE 12

With reference to Sample 12, the treatment procedure of Example 10 is repeated, except that the opened tow is sprayed with water. After the particulate is applied, the water is removed by drying. A superabsorbent, continuous filament web having a 94% loading of superabsorbent polymer particulate adhered to the surface of fibers of the web, is thereby produced. The particulate-loaded web is evaluated as before, and the drip time and results are shown in the Table.

EXAMPLE 13

With reference to Sample 13, the treatment procedure of Example 10 is repeated, except that SANWET® IM 3900F is used. The proportion of additional weight attributable to triacetin and to SAP particulate is estimated as in Example 10, and based thereon, an 80% loading of superabsorbent polymer particulate adhered to the surface of fibers of the web, is found. The particulate-loaded web is evaluated as before, and the drip time and results are shown in the Table. The benefit of decrease in particle size can be observed by an increase in Absorbent Ratio, and also by more rapid absorption as shown by decreased drip time.

COMPARATIVE EXAMPLE

A comparative product of SAP particulate (45%) and a discontinuous cellulose fiber matrix commonly known as "fluff" (55%), indicated as "C-1" in the Table, is similarly evaluated. The drip time and results are shown in the Table.

The present invention may be carried out with various modifications without departing from the spirit or essential attributes thereof, and accordingly, reference should be made to the appended claims, rather than to the foregoing specification, as indicating the scope of the invention.

We claim:

1. A process for making a superabsorbent fiber web comprising the steps of:

providing opened, continuous filament, cellulose ester tow having crimped filaments; and applying superabsorbent polymer particulate and an effective amount of a tackifying agent to said opened tow, said tackifying agent being selected from the group consisting of: acetone, methyl ethyl ketone, methyl acetate, ethyl acetate, propyl acetate, methyl formate, ethyl formate, propyl formate, glacial acetic acid, methylene chloride, tetrahydrofuran, formic acid and mixtures thereof including combinations with a minor amount of other volatile liquids having a boiling point of about 100° C. or less at atmospheric pressures; and cyclohexanone, benyl alcohol, and glycerol derivatives, said glycerol derivatives including glycerol triacetate, triethylglycerol diacetate, and glycol monoethyl ether acetate, whereby there is produced a superabsorbent fiber web comprising said superabsorbent polymer particulate adhered to a surface of said filaments of said tow.

2. The process of claim 1, wherein said superabsorbent polymer particulate is applied subsequent to said tackifying agent.

3. The process of claim 2, wherein said tackifying agent tackifies said tow.

4. The process of claim 2, wherein said tackifying agent tackifies said superabsorbent polymer particulate.

5. The process of claim 1, wherein said superabsorbent polymer particulate and said tackifying agent are simultaneously applied to said opened tow.

6. The process of claim 5, wherein said tackifying agent tackifies said tow.

7. The process of claim 1, wherein said tackifying agent is triacetin.

8. The process of claim 1, wherein said cellulose ester is cellulose acetate.

9. A superabsorbent fiber web for use in an absorbent article, made by the process of claim 1.

10. An absorbent article comprising a continuous filament, cellulose ester web having crimped filaments and loaded with superabsorbent polymer particulate adhered to the surface of said filaments.

11. The absorbent article of claim 10, wherein said loading of said particulate is about 50 to 95 wt. %, based on the combined weight of said particulate and of said filaments.

12. The absorbent article of claim 11, wherein said loading of said particulate is at least about 75 wt. %.

13. The absorbent article of claim 10, wherein said cellulose ester is cellulose acetate.

14. The absorbent article of claim 10, further comprising a non-volatile tackifying agent.

15. The absorbent article of claim 14, wherein said non-volatile tackifying agent is triacetin.

16. The absorbent article of claim 10, further comprising a matrix of discontinuous absorbent fibers.

17. The absorbent article of claim 16 wherein said discontinuous absorbent fibers are cellulosic.

* * * * *